(12) United States Patent
Izadi

(10) Patent No.: US 9,895,206 B2
(45) Date of Patent: Feb. 20, 2018

(54) ADJUSTABLE ORTHODONTIC BRACKET AND METHOD USING A MICROSTRUCTURED SHAPE MEMORY POLYMER SURFACE WITH REVERSIBLE DRY ADHESION

(71) Applicant: Mohammad Izadi, Timonium, MD (US)

(72) Inventor: Mohammad Izadi, Timonium, MD (US)

( * ) Notice: Subject to any disclaimer, the term of this patent is extended or adjusted under 35 U.S.C. 154(b) by 0 days.

(21) Appl. No.: 14/854,198

(22) Filed: Sep. 15, 2015

(65) Prior Publication Data
US 2016/0095672 A1    Apr. 7, 2016

Related U.S. Application Data

(63) Continuation-in-part of application No. 14/659,844, filed on Mar. 17, 2015, now abandoned, and a continuation-in-part of application No. 14/505,531, filed on Oct. 3, 2014, now abandoned.

(51) Int. Cl.
| | | |
|---|---|---|
| *A61C 7/16* | (2006.01) | |
| *A61C 7/14* | (2006.01) | |
| *A61C 1/00* | (2006.01) | |

(52) U.S. Cl.
CPC ............ *A61C 7/16* (2013.01); *A61C 7/146* (2013.01); *A61C 1/0046* (2013.01)

(58) Field of Classification Search
CPC .............. A61C 7/14; A61C 7/146; A61C 7/16
USPC .................................................. 433/8, 9, 10
See application file for complete search history.

(56) References Cited

U.S. PATENT DOCUMENTS

| | | | | |
|---|---|---|---|---|
| 4,193,195 A | * | 3/1980 | Merkel | A61C 7/12 433/13 |
| 4,243,387 A | | 1/1981 | Prins | |
| 4,256,455 A | * | 3/1981 | Forster | A61C 7/12 433/8 |
| 4,284,405 A | | 8/1981 | Dellinger | |
| 4,487,581 A | | 12/1984 | Adler | |
| 4,597,739 A | | 7/1986 | Rosenberg | |
| 4,659,309 A | * | 4/1987 | Merkel | A61C 7/12 433/16 |
| 4,799,883 A | * | 1/1989 | Stoller | A61C 7/12 433/11 |
| 5,018,259 A | * | 5/1991 | Wildman | A61C 7/12 216/33 |
| 5,088,923 A | * | 2/1992 | Andreiko | A61C 7/12 433/9 |
| 5,154,606 A | * | 10/1992 | Wildman | A61C 7/12 433/8 |
| 5,238,404 A | * | 8/1993 | Andreiko | A61C 7/12 433/20 |

(Continued)

*Primary Examiner* — Nicholas Lucchesi
(74) *Attorney, Agent, or Firm* — Hauptman Ham, LLP

(57) ABSTRACT

An adjustable orthodontic bracket includes a metal base adapted to be rigidly secured directly to a tooth by a relatively thin layer of an orthodontic adhesive. This relatively thin layer of heat softening material fastens an orthodontic bracket directly to a tooth and subsequently heats the orthodontic material with a digital laser that allows the polymer material to reproduce a liquidous surface for adjusting the position of the bracket so that the bracket can be adjusted in all directions around the base member without overlapping the periphery of the base member.

6 Claims, 5 Drawing Sheets

(56) References Cited

U.S. PATENT DOCUMENTS

| | | | | |
|---|---|---|---|---|
| 5,552,177 | A * | 9/1996 | Jacobs | A61C 7/16 427/2.29 |
| 5,711,665 | A * | 1/1998 | Adam | A61C 19/004 433/24 |
| 5,735,688 | A * | 4/1998 | Razdolsky | A61B 17/663 433/181 |
| 5,993,206 | A * | 11/1999 | Andreiko | A61C 7/146 433/24 |
| 6,017,216 | A * | 1/2000 | DeLeo | A61C 7/16 433/9 |
| 6,090,867 | A * | 7/2000 | Starling, Jr. | A61K 6/0023 523/113 |
| 8,026,296 | B2 * | 9/2011 | Kalgutkar | A61K 6/0061 433/10 |
| 8,038,438 | B2 * | 10/2011 | Ruiz Diaz | A61C 7/14 433/11 |
| 8,371,846 | B2 | 2/2013 | Kishi | |
| 8,550,814 | B1 | 10/2013 | Collins | |
| 2003/0170584 | A1 * | 9/2003 | Andreiko | A61C 7/14 433/9 |
| 2010/0210745 | A1 * | 8/2010 | McDaniel | C09D 5/008 521/55 |
| 2011/0212406 | A1 * | 9/2011 | Jensen | A61K 6/0023 433/3 |
| 2015/0017596 | A1 * | 1/2015 | Wong | A61C 7/143 433/9 |

\* cited by examiner

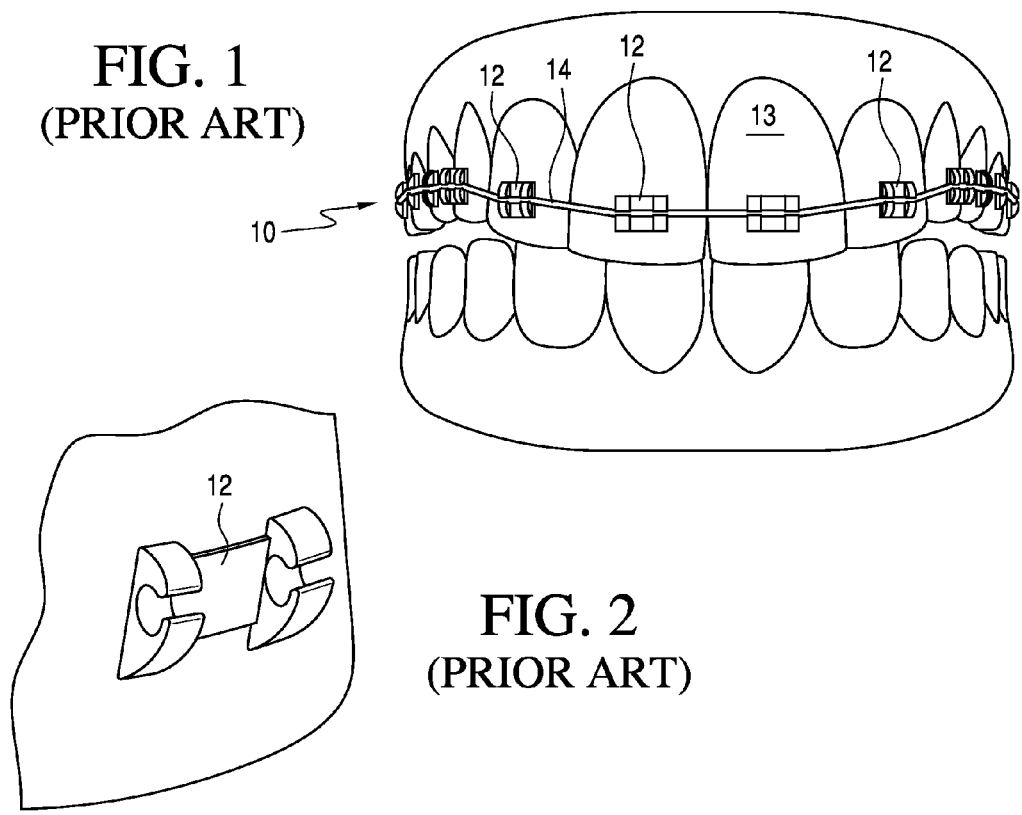
FIG. 1 (PRIOR ART)
FIG. 2 (PRIOR ART)
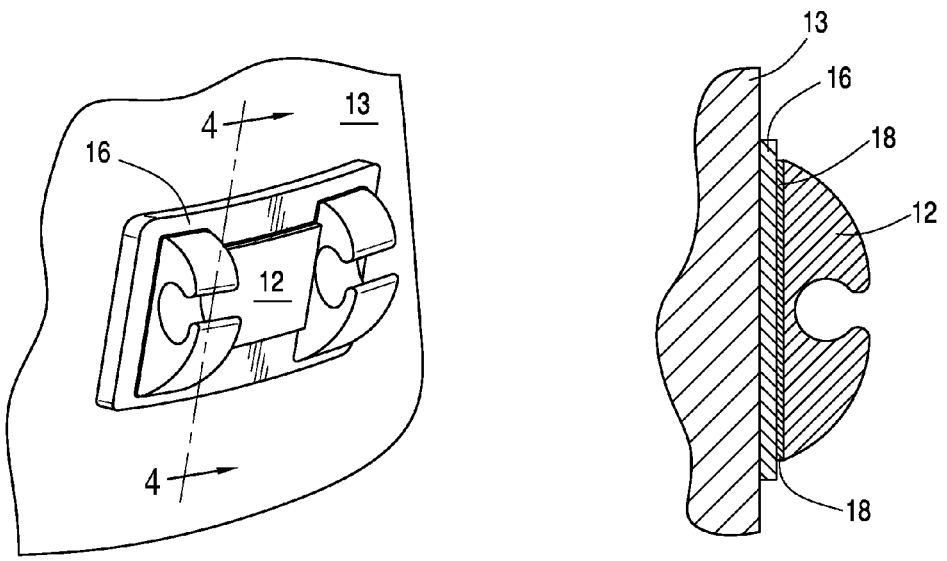
FIG. 3
FIG. 4

ADJUSTABLE ORTHODONTIC BRACKET AND METHOD USING A MICROSTRUCTURED SHAPE MEMORY POLYMER SURFACE WITH REVERSIBLE DRY ADHESION

CROSS REFERENCE TO RELATED APPLICATIONS

The present application is a second Continuation-In-Part of U.S. patent application Ser. No. 14/505,531, filed on Oct. 3, 2014, and a first Continuation-In-Part of U.S. patent application Ser. No. 14/659,844, accorded a filing date of Mar. 17, 2015, and priority is hereby claimed under 35 U.S.C. §120 based on these applications and are hereby incorporated by reference in their entirety into the present application.

FIELD OF THE INVENTION

This invention relates to an adjustable orthodontic bracket and a method for adjusting an orthodontic bracket without breaking a bond between a patient's tooth and the bracket.

BACKGROUND FOR THE INVENTION

The practice of orthodontics requires a considerable amount of chair time with patients so that perfect or near perfect alignment of the patient's teeth can be achieved. When orthodontic brackets (braces) are bonded to the patient's teeth at an initial treatment, it is very difficult if not impossible to precisely position each bracket. The problem is exacerbated by a number of issues. For example, excess crowding of the teeth, angulations of the teeth, lack of access and at times human error or inability to precisely position a bracket on a specific tooth.

A further problem confronting the orthodontist is that the realignment of the teeth following the initial treatment, it becomes apparent that some of the brackets that have been bonded to a patient's teeth need to be repositioned.

This requires removal of the originally bonded bracket from the tooth enamel that causes pain and discomfort, frequently damages the bracket, requires a new bracket, requires removal of the existing bonding material on the patient's teeth, repairing the tooth surface and rebonding a new bracket in the ideal position. This procedure is costly, time consuming and may not necessarily be the last time the orthodontist is replacing that bracket.

After many years, it is still common practice to adhesively bond an orthodontic bracket directly onto a tooth. Nevertheless, there have been attempts to provide adjustable orthodontic brackets. For example, a U.S. Pat. No. 4,243,387 of Prins discloses an Adjustable Orthodontic Bracket that can be fixed to a band to surround a tooth. The bracket has a base to be carried by the tooth, and a movable member to which wires are attached, and a retainer to fix the movable member to the base. In the preferred embodiment, the base and the movable member have spherical surfaces so that motion of the movable member can dispose the bracket at any desired angle in any plane for the desired torque, and in all embodiments the movable member is rotatable about the retainer through 360 degrees and can be set at any desired angle.

A U.S. Pat. No. 4,487,581 of Adler discloses an Orthodontic Bracket. As disclosed therein, an improved orthodontic bracket is formed of a wire gripping block secured within a spring metal base having wings or string tabs which set within tab receiving slots on opposite ends of the block. A slot within the face of the block is configured for gripping an orthodontic banding or archwire extending from tooth to tooth, the face being large enough to accommodate any desired orientation of the slot to convert tension forces in the wire to a desired amount of torque for inducing a predetermined rotation of the tooth. A central plate portion of the base includes a slot elongated for the guidance of an orthodontic pin between the block and the base while transverse wing portions of the aperture serve as keyways for cooperation with alignment pins extending from a back face of the block. A channel for receipt of the orthodontic pin is also located on the back face of the block. Further, a bifurcated shim having legs contacting cam surfaces of the block for insertion between the block and the base to facilitate removal of the block for interchanging with other blocks, the legs passing outside the alignment pins and one of the tabs, the one tab having peripheral slots for engagement with the legs.

A more recent Kishi U.S. Pat. No. 8,371,846 discloses a Self-Adjustable Self-Ligating Orthodontic Bracket. As disclosed, a self-adjustable, self-ligating orthodontic bracket includes a base with a tooth face bonded to a surface of a tooth. A linking body includes a body connection. The linking body is in physical communication with an archwire transmitting a force to the linking body. A connector applies a tension between the linking body and the base motivating the linking body and the base toward a normal position.

Notwithstanding the above, it is presently believed that there is a need and a potential commercial market for an adjustable orthodontic bracket and method in accordance with the present invention. There should be a commercial market for such devices because they use a base member adhesively bonded to a tooth instead of adhesively bonding the orthodontic bracket on the tooth as commonly done today. The base member has dimensions and configuration that is slightly larger than the bracket. Therefore, the bracket is heat softenable material onto the base member and the base member is adhesively bonded to the tooth. A laser with pinpoint accuracy softens the heat softenable material in order to adjust the bracket.

In addition, the adjustable orthodontic bracket and method are considerably more cost effective, safe, saves hours of an orthodontist's time, relieves a patient from pain and discomfort, and reduces the costs for such treatments.

SUMMARY OF THE INVENTION

Briefly, an adjustable orthodontic bracket in accordance with the present invention includes a metal base member adapted to be rigidly secured directly to a tooth by a thin layer of an orthodontic adhesive. Further, a relatively thin layer of lead free heat softenable material for joining two surfaces rigidly together is provided together with an orthodontic bracket having a base to fit within a surface area of the base member and an engagement receiver for an archwire by which forces are developed in a patient's mouth. In the device in accordance with the invention, the base member overlaps the base of the bracket surrounding the base so that the bracket can be adjusted in all directions around the base member without overlapping the periphery of the base member.

In addition, the adjustable orthodontic bracket and method are considerably more cost effective, safe, saves hours of an orthodontist's time, relieves a patient from pain and discomfort, and reduces the costs for such treatments.

Briefly, an adjustable orthodontic bracket in accordance with the present invention includes a metal base member adapted to be rigidly secured directly to a tooth by a thin layer of an orthodontic bonding material or adhesive. Further, a relatively thin layer of lead free heat softenable material for joining two surfaces rigidly together is provided together with an orthodontic bracket having a base to fit within a surface area of the base member and an engagement receiver for an archwire by which forces are developed in a patient's mouth. In the device in accordance with the invention, the base member overlaps the base of the bracket surrounding the base so that the bracket can be adjusted in all directions around the base member without overlapping the periphery of the base member.

A further embodiment of the invention contemplates a method for adjusting an orthodontic bracket without breaking a bond between a patient's tooth and a base of an orthodontic bracket. The method comprises the following steps.

Providing a thin layer of an orthodontic adhesive and a metal base member adapted to be rigidly secured directly to a tooth by a thin layer of orthodontic bonding material or adhesive. In addition, a layer of heat softenable material wherein the surface of the heat softenable material reaches a liquidous stage under heat for bonding two surfaces rigidly together. In a preferred embodiment of the invention it is important that an adjustment may be made by sliding or translation of the orthodontic bracket on the base member i.e. with respect to the tooth.

In addition, an orthodontic bracket having a base and wherein the base of the bracket does not overlap the base member. In other words, the base member overlaps the base of the bracket by between 0.5 mm and up to about 1.0 mm on each side thereof so that the bracket can be adjusted by an amount of up to about 1.0 mm in each planar direction without overlapping the base member i.e. the surface area of the tooth. The bracket can also be adjusted rotationally about the base member without exceeding the periphery of the base member. However, with shape memory movement of the bracket it may be limited to a distance equal to the thickness of the bonding material.

In addition to the above, a diode laser is provided to generate heat of about 138° C. A cordless micro laser identified as StylaOrtho (diode laser) from Zap Dental of Pasedena, Calif. is an example of an appropriate laser.

The invention also contemplates a method of fastening a base member directly to a patient's tooth and bonding the bottom surface of the base member to the tooth. Further, a thin layer of heat softenable or bonding material that reaches a liquidous state and heating the heat softenable material to form a liquidous plane between the base of the bracket and the softenable material. Further, after heating the heat softenable material to a liquidous state the position of the bracket with respect to adjacent teeth and for positioning an archwire is adjusted using the tip of the laser to move the bracket.

Still further, the heat is removed by a pinpoint heat from a diode laser, removed and the softenable material is hardened to properly position the bracket.

A further embodiment of the invention contemplates a method for temporarily and/or permanently affixing a bracket to a human tooth with a reversible bonding material. The method comprises or consists of the following steps.

Providing a foreign body (a dental bracket or retainer for holding and positioning an arch wire to assert force to move a tooth by asserting a force thereon) having a surface that generally conforms with the surface of a human tooth and providing a mass of a reversible bonding material namely a micro structured shaped memory polymer surface with reversible dry adhesion as disclosed in an article entitled "Microstructured Shape Memory Polymer Surface with Reversible Dry Adhesion," authored by Jeffery D. Eisenhaure, Tao Xie, Stephen Varghese and Seok Kim that was published on Aug. 14, 2013, and is incorporated herein in its entirety by reference.

The aforementioned article presents a shape memory polymer (SMP) surface with a repeatable, very strong (>18 atm), and extremely reversible (strong to weak adhesion ratio of >10,000) dry adhesion to a glass substrate. This was achieved by exploring bulk material properties of SMP and surface microstructuring. Its exceptional dry adhesion performance is attributed to the SMP's rigidity change in response to temperature and its capabilities of temporary shape locking and permanent shape recovery, which when combined with a micro-tip surface design enables time-independent control of contact area.

In conclusion it is stated that " . . . shape memory polymers can offer excellent dry adhesive performance by virtue of their shape fixing-recovery properties, and dramatic shift in ELASTIC modulus in response to temperature shape . . . " In another area it states " . . . our particular SMP adhesive demonstrates tensile adhesive strength to glass twenty times greater than the typically cited shear adhesion of gecko foot pads (about 10 N/cm×cm)" making the material a great consideration for dental adhesives.

It is presently Applicant's belief that the material disclosed therein can be used for cementation of temporary and permanent crowns, inlays, onlays, and cosmetic veneers to human teeth as well as implants. Quite often, removing crowns and veneers is a major issue in dentistry which application of heat can soften the material for the ease in removal. Applicant further believes that a laser can accomplish the heat transfer very precisely and locally without affecting the pulp of the tooth or other soft tissue structures in the mouth.

The major components of the materials are as follows:
1) EPON 826 (The diglycidyl ether of bisphenol A epoxy monomer; Momentive). Available at Resolution Performance Products of Houston, Tex. 77210 U.S.A.
2) Jeffamine D230 (Poly(propylene glycol) bis (2-aminopropyl) ether; Huntsman). Available from Huntsman Petrochemical Corporation of Houston, Tex. 77227-7707 U.S.A.
3) NDGE (Neopentyl glucol diglycidyl ether, TCI America). Available from TCI America with a main office in Portland, Oreg.

Further details on a microstructured shape memory polymer surfaces with reversible dry adhesion is disclosed in an article by Jeffery D. Eisenhaure, Tao Xie, Stephen Varghese and Seok Kim as reported in an ACS publication by the 2013 American Chemical Society which is incorporated herein in its entirety by reference.

The invention will now be described in connection with the accompanying drawings wherein like numbers are used to indicate like elements.

DESCRIPTION OF THE DRAWINGS

FIG. 1 is a schematic illustration of a prior art bracket assembly attached directly and securely to a patient's tooth and an archwire applying forces to an individual's teeth;

FIG. 2 is a perspective view of a prior art orthodontic bracket bonded directly to the surface of an individual's tooth;

FIG. 3 is a perspective view of an orthodontic bracket attached to a base member which is attached to a tooth in accordance with the present invention;

FIG. 4 is a cross-sectional view of an adjustable orthodontic bracket in accordance with the invention;

DESCRIPTION OF THE PREFERRED EMBODIMENTS OF THE INVENTION

Figure 5:
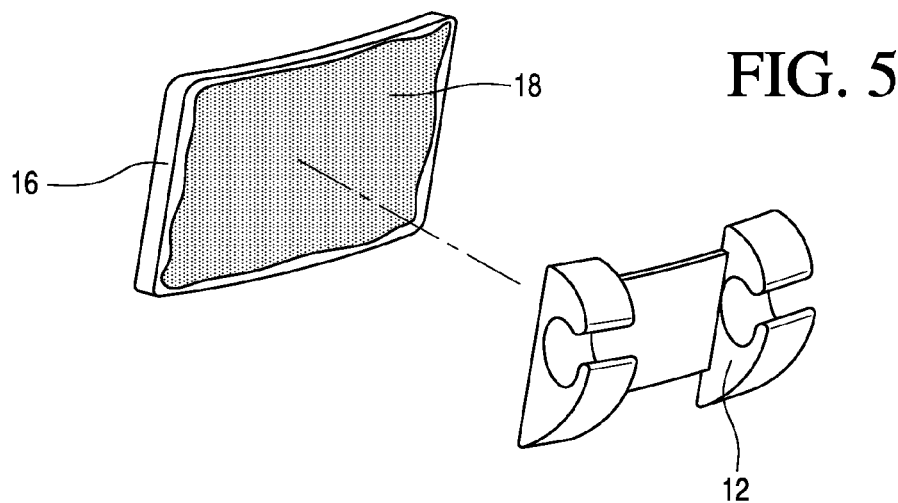
FIG. 5 is a partially exploded view of a base member and solder layer as used in a preferred embodiment of the invention.

As illustrated, in FIG. 1 a set of orthodontic braces 10 includes a plurality of orthodontic brackets 12 and an archwire 14 for applying forces to reposition the upper teeth in a patient's mouth. As shown in FIG. 1, the orthodontic brackets 12 are directly bonded to the surfaces of a patient's upper teeth. The latter feature is more clearly shown in FIG. 2 wherein a single bracket 12 is securely bonded to a single tooth by an orthodontic bonding material or adhesive. Bonding materials commonly used in orthodontics to adhere a bracket to a tooth surface are composite resins such as Transbond XT (Ref 712-036 manufactured by 3M Unitek), or other similar products manufactured by Ormco, Densply or Reliance, or thermoplastic materials.

For contrast, FIG. 3 illustrates a base member 16 preferably of metal that is bonded directly to a tooth by a thin layer of an orthodontic adhesive and is positioned between a relatively flat base of the orthodontic bracket 12 and the tooth 13. It should be recognized that the tooth engaging side of the base member 16 may have a slight curvature to more closely conform to the shape of a tooth, and also may include a ridged surface to enhance its bonding functionality, similar to that of the ridged or cross-hashed surface of the bracket itself.

A feature of the present invention resides in a heat softenable layer of a bonding polymeric material that has a liquidous phase on its surface that allows the orthodontic bracket 12 to be moved linearly or rotationally and is also supported by applying heat. For example, a lead-free solder is one operable example while a special thermoplastic material developed for this purpose is contemplated and considered promising. As illustrated in FIG. 4, there is a slight overlap of the base of the bracket 12 by the base member 16 to allow for free movement within the confines of the base member. The softenable layer 18 and bracket 12 should not overlap the base member 16 to avoid forming a cavity that would trap food or drink.

As illustrated in FIG. 5, a layer of heat softenable material such as a lead-free solder that melts at about 138° C. or as low as about 120° C. is disposed between a relatively flat base of the bracket 12 and the base member 16. These assemblies are most likely manufactured in a manufacturer's plant and provided to an orthodontist for use in their practice.

Figure 6:
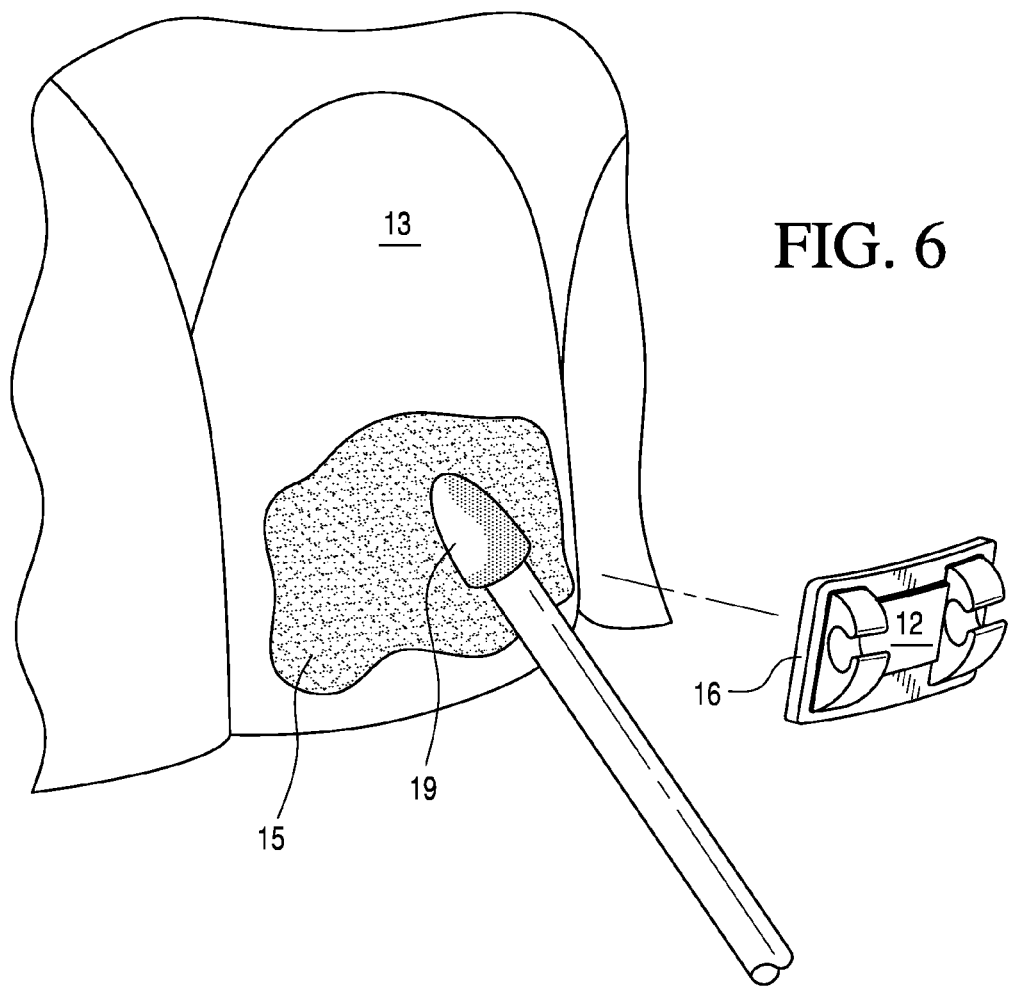
FIG. 6 is a schematic illustration of the step of applying an orthodontic adhesive being applied to the surface of a tooth and an orthodontic bracket assembly.

For contrast FIG. 6 illustrates an adhesive applicator 19 for applying a conventional orthodontic adhesive 15 on a surface of a tooth for bonding a base member 16 to the tooth 13. As shown the bracket 12 has already been attached to the base member 16. The best known material to bond the bracket base to a sub-base is lead-free solder, however a specially compounded thermoplastic material is promising.

Figure 7:
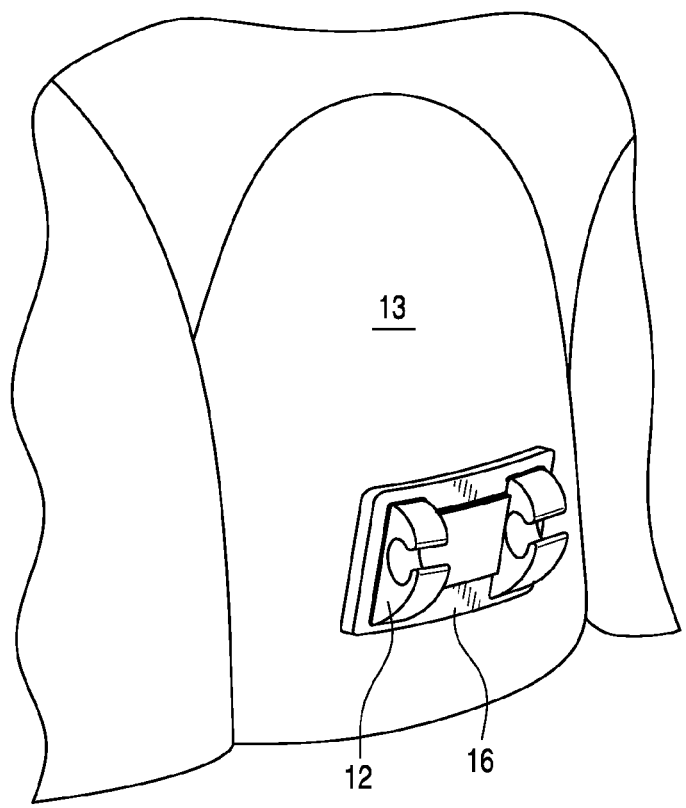
FIG. 7 is a schematic illustration of a base member and bracket assembly including a base member in accordance with the invention.
Figure 8:
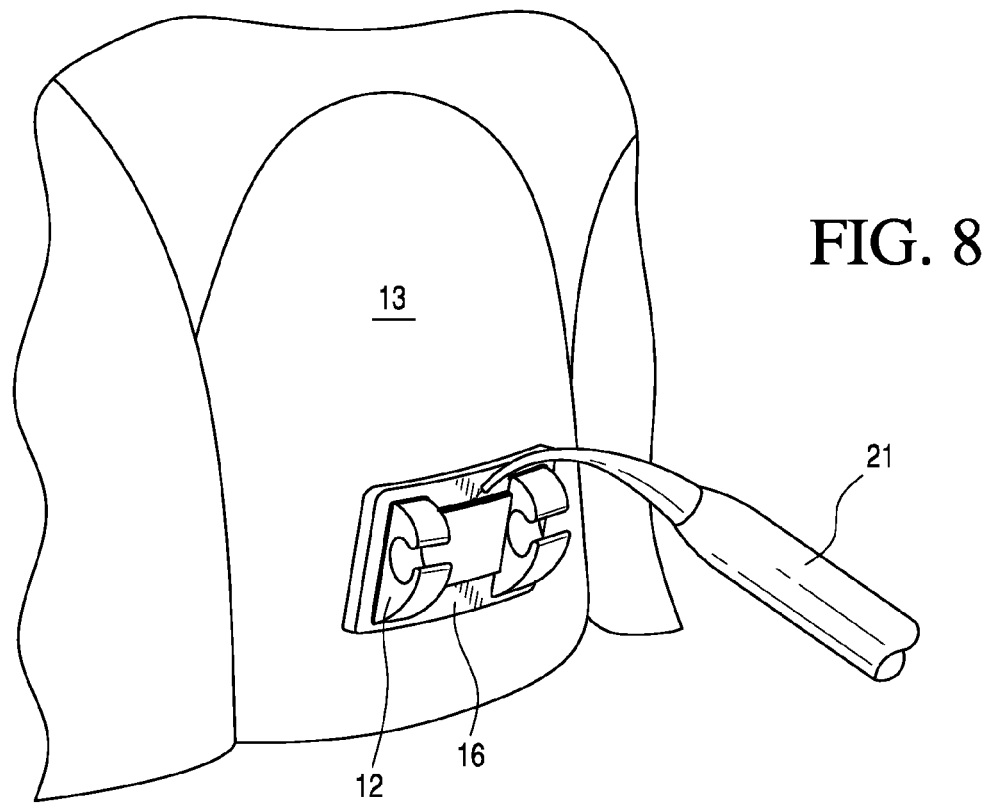
FIG. 8 is a schematic illustration of a base member attached to a tooth and a diode laser for softening the solder prior to repositioning of a bracket.

An orthodontic bracket 12 and base member 16 are bonded to a tooth 13 as shown in FIGS. 7 and 8. FIG. 7 illustrates an initial position of a bracket. FIG. 8 illustrates a pinpoint diode laser for heating the heat softenable layer 18 between the bracket 12 and base member 16 with a diode laser for creating a liquidous phase between the base of the bracket and the tooth at about 138° C. or less and perhaps as low as about 90° C.

Figure 9:
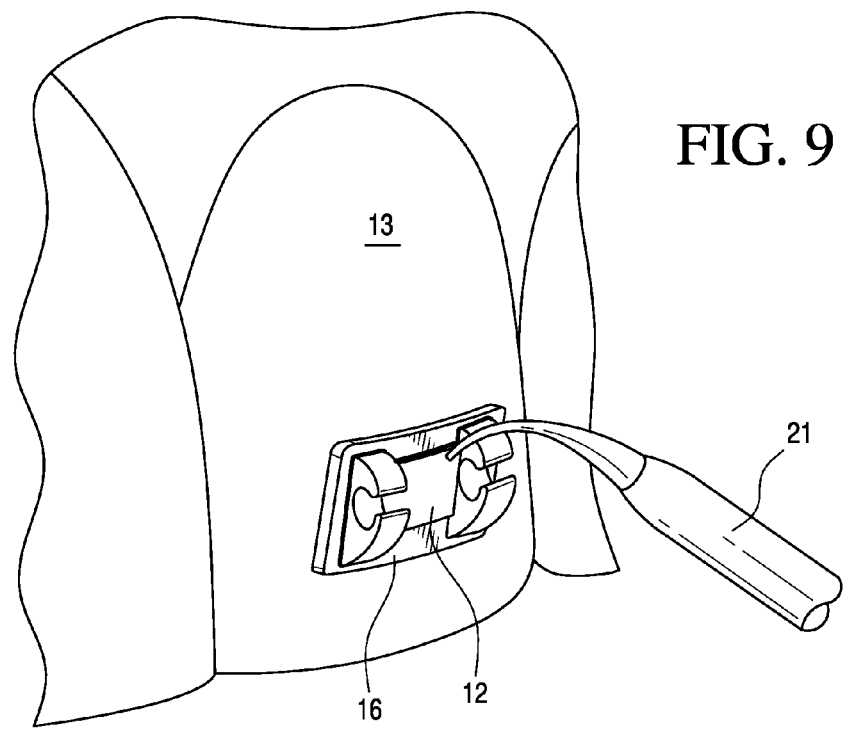
FIG. 9 is a schematic illustration showing the use of a tip of a laser to reposition an orthodontic bracket on a base member.
Figures 10, 11:
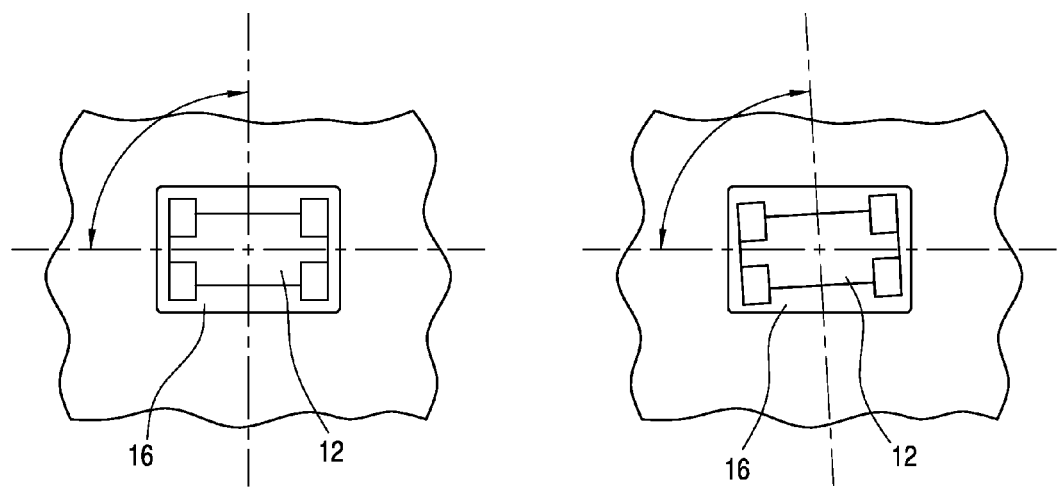
FIG. 10 is a schematic illustration of an orthodontic bracket on a base member attached to a tooth before adjustment.
FIG. 11 is a schematic illustration of a tooth and base member shown in FIG. 10 but after readjustment of the bracket on the base member.
Figure 12:
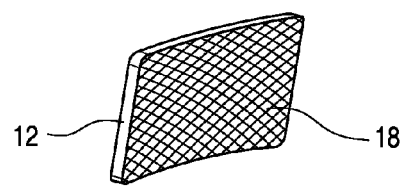
FIG. 12 is a perspective view of a base member and a thin layer of solder thereon.

As illustrated in FIG. 9 the tip of a laser 21 is used to adjust the positions of an orthodontic bracket 12 on a tooth 13 when the heat softenable layer 18 is in a liquidous stage. For example, FIG. 10 shows an original position of a bracket 12 while FIG. 11 illustrates a slight rotation adjustment of the bracket 12. The best way to move a bracket is to move the bracket with the tip of the laser which may be a bit thicker than usual to facilitate this approach.

Figures 13, 14:
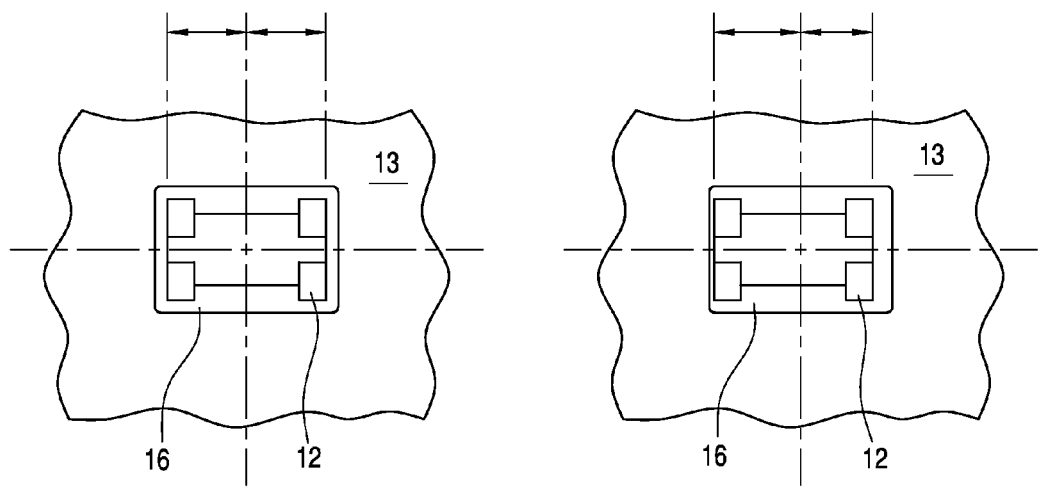
FIG. 13 is a schematic illustration of a base member positioned on a tooth and bracket before adjustment.
FIG. 14 is a schematic illustration of the base member and bracket after linear adjustment to the left.

For contrast, FIG. 13 illustrates the position of an orthodontic bracket 12 fixed to a base member 16 on a tooth 13 in an initial position while FIG. 14 illustrates a similar bracket 12 fixed by a base member 16 to a tooth 13 but with a linear adjustment by a small movement to the left or the right.

It presently appears to Applicant that an adjustable orthodontic bracket assembly that includes a heat reversible polymer adhesive deposited onto a patient's tooth for fixing an orthodontic engagement receiver is a promising embodiment of the invention. Applicant also believes that the material disclosed herein namely a miscible blend of poly (ε-caprolactone) (PCL) and diglycidyl ether of bisphenol-A/diaminodiphenylsulfone (DGEBA/DDS) epoxy processed to a unique morphology via polymerization-induced phase separation (PIPS) that is safe i.e. from toxic effects as well as the effects of carcinogens. However, such material has not yet been given approval by the U.S. Food and Drug Administration (FDA). Nevertheless, if approval is not given there are known modifications of the disclosed composition that should be safe to use.

In one embodiment of the invention the bracket is combined with a base member that is attached to a tooth by an FDA approved reversible dental adhesive. Nevertheless, there are advantages in attaching the bracket directly to a tooth with a heat reversible bonding material.

It is further believed that there is an advantage in using a base member that is slightly contoured to coincide with the curvature of a tooth's surface. A still further embodiment of the invention incorporates an epoxy reversible adhesive and/or a nano-structural thermally reversible adhesive. For example, a miscible blend of poly(ε-caprolactone) (PCL)

and diglycidyl ether of bisphenol-A/diaminodiphenylsulfone (DGEBA/DDS) epoxy processed to a unique morphology via polymerization-induced phase separation (PIPS) as described in an article entitled "A Thermally Responsive, Rigid, and Reversible Adhesive," by Xiaofan Luo, Kathryn E. Lauber and Patrick T. Mather, Polymer 51 (2010), 1169-1175 at Science Direct (ELSEVIER), www.elsevier.com/locate/polymer contains further details on the above adhesive and which is incorporated herein in its entirety by reference.

A further embodiment of the invention relates to a method for adjusting an orthodontic bracket assembly on a patient's tooth. The method comprises or consists of the following steps. Providing an orthodontic engagement receiver for receiving an archwire by which orthodontic forces are applied to a patient's tooth to thereby move the tooth.

In the presently preferred embodiment of the invention, a method for temporarily and/or longer term affixing a foreign body to a human tooth with a reversible polymeric adhesive comprises or consists of the following steps. The first step includes providing a foreign body having a surface that generally conforms with the surface of a human tooth and a mass of a reversible polymeric bonding material. A thin layer of the reversible bonding material is formed into a layer directly onto a tooth wherein the thin layer of reversible bonding material forms a conforming layer directly on the tooth. Heating the bonding material in excess of a softening temperature and applying a metal dental bracket or retainer directly onto the surface of the tooth. The layer is heated with a diode laser and heated in excess of its temperature to form a bond and then allowed to cool to reach a temperature below its softening temperature to return to the rigid set for affixing the body directly to the tooth. In this form the bracket is fixed to the tooth and movable on a liquidous (heated) surface which allows the bracket to be adjusted in its position on the tooth. The bracket is moved by initiating movement of the tooth by braces and subsequently the bonding material is heated to form a liquid surface and then returned to a glass-like bond. After softening the bonding material and the bracket are repositioned and allowed to solidify into a more permanent type of bond. In this form of the invention, the bonding material is a microstructured shaped memory polymer surface with a reversible dry adhesion as disclosed in the article by Jeffery D. Eisenhaure, Tao Xie, Stephen Varghese and Seok Kim as described above.

Three examples are listed above. As indicated in the article, a shaped memory polymer (SMP) surface with repeatable, very strong (>18 atm), and extremely reversible (strong to weak adhesion ratio of >10,000) dry adhesion to a glass substrate. This was achieved by exploring bulk material properties of SMP and surface microstructuring. Its exceptional dry adhesion performance is attributed to the SMP's rigidity change in response to temperature and its capabilities of temporary shape locking and permanent shape recovery, which when combined with a micro-tip surface design enables time-independent control of contact area.

With respect to the above, the shape memory polymer is selected from the group consisting of bisphenol A/epichlorohydrin based epoxy, polyoxylenediamine and neopentyl glucol diglycidyl ether.

In the above embodiment of the invention a thin layer of a reversible bonding adhesive material is in both a rigid and a reversible adhesive in which the epoxy forms highly interconnected spheres that are interpenetrated with a PCL matrix. When heated to melt the PCL (60° C.<T<200° C.) the epoxy remains rigid due to the high epoxy $T_g$ (>200° C.) while PCL liquefies to become a melt adhesive.

In a preferred embodiment of the invention, the bonding material is a polymeric adhesive selected from the group of bisphenol A/epichloro hydrin based epoxy available in the commercial market as EPON® 828 and available from Resolution Performance Products of Houston, Tex. 77210, U.S.A. Jeffamine® D230 available from Huntsman Petrochemical Corporation of Houston, Tex. 77227-7707, U.S.A. which is Poly oxypropylenediamene and NDGE Neopentyl glucol diglycidyl ether available from TCI America with main office in Portland, Oreg., U.S.A.

While the invention has been described in connection with its preferred embodiments it should be recognized that changes and modifications may be made therein without departing from the scope of the appended claims.

What is claimed is:

1. A method for affixing a dental bracket having a base member directly to a human tooth for an initial period of time and for repositioning and re-bonding the dental bracket on said tooth, comprising the following steps:
   providing a dental bracket and an archwire that fits within said dental bracket for applying a force against said bracket to thereby straighten said tooth;
   applying a thin layer of a reversible bonding material on said tooth, with said thin layer of bonding material generally conforming to the shape of said tooth;
   heating the bonding material to a temperature to soften the bonding material;
   attaching said bracket to said tooth;
   allowing the bonding material to form a rigid glass-like bond;
   re-heating the bonding material to provide a liquid surface;
   adjusting said bracket on said tooth to align a guidance to direct the direction of force to straighten said tooth;
   allowing the bonding material to return to a rigid glass-like bond;
   wherein said bonding material is a microstructured shaped memory polymer surface with a repeatable very strong greater than 18 atm and extremely reversible strong to weak adhesion ratio of >10,000 dry adhesion to a glass substrate; and
   wherein said base member is slightly contoured to coincide with the curvature of the surface of said tooth.

2. The method for affixing a dental bracket according to claim 1, further comprising selecting said layer of reversible bonding material from the group consisting of bisphenol A/epichilorohydrin based epoxy, polyoxypropylene diamine and neopentyl glucol diglycidyl ether.

3. The method for affixing a dental bracket according to claim 1, further comprising forming said reversible bonding material from a miscible blend of poly(ε-capralactone) (PCL) and didyl ether of bisphenol A/diaphenol sulfone (DGEBA/DDS) epoxy.

4. The method for affixing a dental bracket according to claim 1, wherein the bonding material is a bisphenol A/epichilorohydrin based epoxy resin bonding material.

5. The method for affixing a dental bracket according to claim 1, wherein the bonding material is a polyoxypropylene diamine bonding material.

6. The method for affixing a dental bracket according to claim 1, wherein the bonding material is a neopentyl glucol diglycidyl ether bonding material.

* * * * *